(12) United States Patent
Proksa (10) Patent No.: US 7,933,378 B2
(45) Date of Patent: Apr. 26, 2011

(54) MULTI-TUBE X-RAY DETECTION (75) Inventor: Roand Proksa, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 162 days.

(21) Appl. No.: 12/377,921

(22) PCT Filed: Jul. 24, 2007

(86) PCT No.: PCT/US2007/074207
§ 371 (c)(1),
(2), (4) Date: Feb. 18, 2009

(87) PCT Pub. No.: WO2008/024586
PCT Pub. Date: Feb. 28, 2008

(65) Prior Publication Data
US 2010/0166140 A1 Jul. 1, 2010

Related U.S. Application Data (60) Provisional application No. 60/823,509, filed on Aug. 25, 2006.

(51) Int. Cl.
A61B 6/00 (2006.01)
(52) U.S. Cl. .......................................................... 378/9
(58) Field of Classification Search ................ 378/9
See application file for complete search history.

(56) References Cited

U.S. PATENT DOCUMENTS

| 5,068,882 | A | 11/1991 | Eberhard |
| 5,625,661 | A | 4/1997 | Oikawa |
| 6,421,412 | B1 | 7/2002 | Hsieh et al. |
| 6,490,333 | B1 | 12/2002 | Hsieh |
| 2004/0081270 | A1* | 4/2004 | Heuscher ........................ 378/4 |
| 2005/0074094 | A1 | 4/2005 | Jen et al. |
| 2005/0135550 | A1 | 6/2005 | De Man et al. |
| 2005/0190878 | A1 | 9/2005 | De Man et al. |
| 2006/0050841 | A1 | 3/2006 | Distler et al. |

FOREIGN PATENT DOCUMENTS

| WO | 2006038145 A1 | 4/2006 |
| WO | 2006051467 A2 | 5/2006 |

* cited by examiner

Primary Examiner — Courtney Thomas (57) ABSTRACT

A computed tomography system (100) includes a first ($108_1$) and a second source ($108_N$) disposed at different z-axis locations at about a same angular position around an examination region (112) that alternately emit radiation beams (114) that traverse the examination region (112). The first source ($108_1$) emits a first radiation beam ($114_1$) having a first outer projection (204) and the second source ($108_N$) emits a second radiation beam ($114_N$) having a first outer projection (216). Both of the first outer projections (204, 216) traverse plane perpendicular to the axis of rotation, and the first outer projections (204, 216) define a width of a volume (400) within which the emitted radiation beams (114) are confined. A common detector (124) detects radiation from the x-ray beams (114) that traverses the volume (400) and generates data indicative thereof, and a reconstructor (132) reconstructs the data to generate an image of the volume (400).

23 Claims, 7 Drawing Sheets

MULTI-TUBE X-RAY DETECTION

CROSS REFERENCE TO RELATED APPLICATIONS

This application claims the benefit of U.S. provisional application Ser. No. 60/823,509 filed Aug. 25, 2006, which is incorporated herein by reference.

The present application relates to imaging systems, including medical imaging systems, baggage inspection systems, non-destructive testing systems, and the like. It finds particular application to computed tomography (CT) and, more particularly to multi-tube CT imaging.

Conventional cone beam CT systems have large-area two-dimensional or multi-slice detectors. Such detectors are used to scan relatively larger volumes relative to one-dimensional or single-slice detectors when using axial scan protocols. However, cone beam axial data acquisitions are limited in that they fail to adequately sample portions of the scanned or imaged volume. As a result, only a subset of the scanned volume can be reconstructed.

Figure 7:
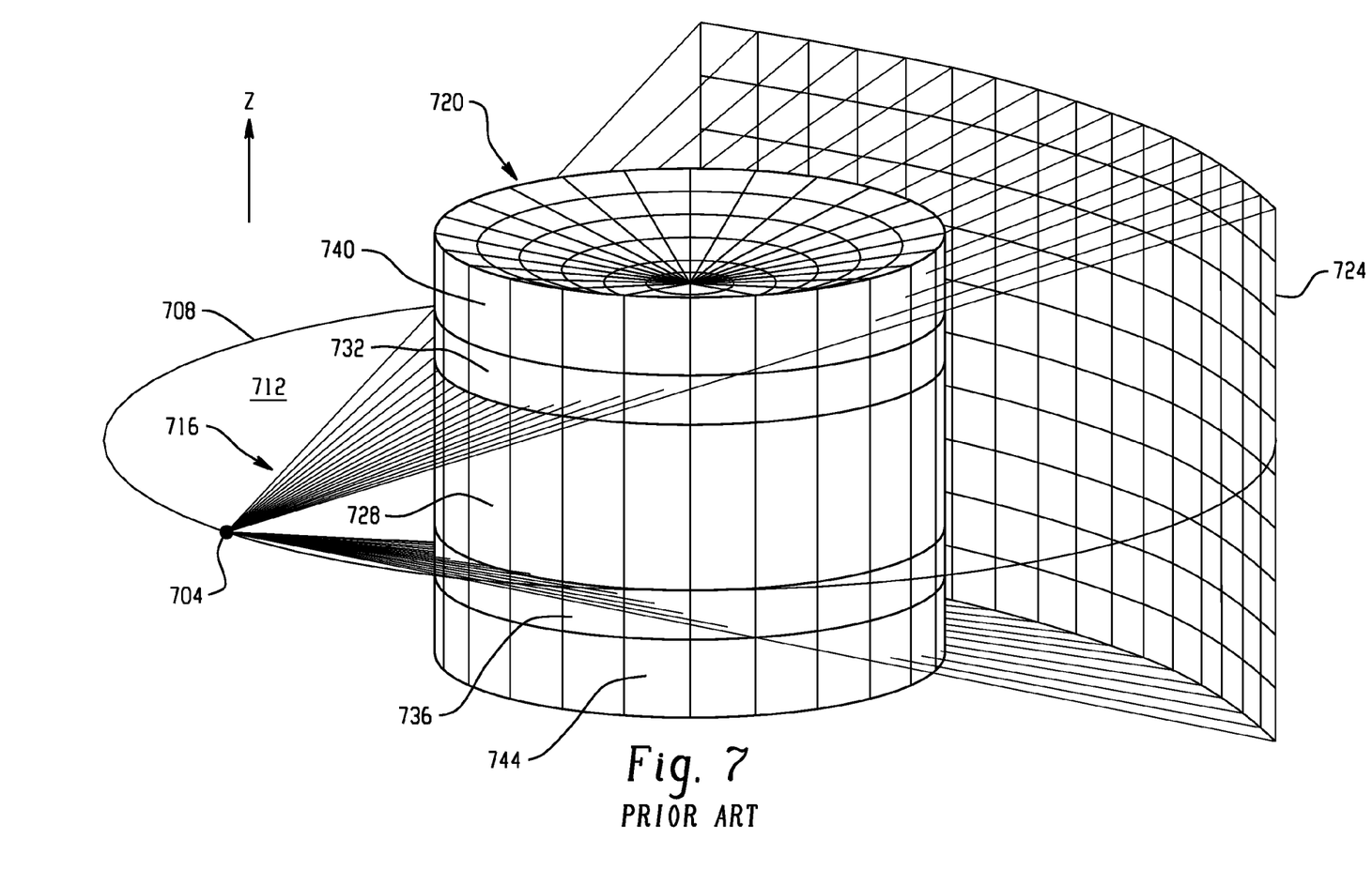
FIGS. 7 and 8 illustrate conventional cone beam CT beam geometry.

This is illustrated in FIG. 7, which shows a cone beam radiation source 704 that moves along a trajectory 708 about an examining region 712, a cone beam 716, a volume 720 within the examination region 712 that is irradiated by the cone beam 716, and detectors 724 that detect the radiation that traverses the volume 720. As depicted, the geometry of the cone beam 716 is configured so that the beam 716 substantially illuminates the width of the detector 724 in a z-direction. With this configuration, the beam 716 fails to irradiate portions of the volume 720 at each angular sampling position as the source 704 moves along the trajectory 708.

By way of example, imagine partitioning the volume 720 into regions 728, 732, 736, 740, and 744. The region 728 represents a volume that is always illuminated by the cone beam 716 as the source 704 travels along the trajectory 708. As a result, the detected data indicative of the region 728 includes 360 degrees of data. Such data can be reconstructed since 180 degrees plus a fan angle worth of data is required for reconstruction purposes. This data is also suitable for retrospective cardiac CT applications since an arbitrary 180 degrees worth of data can be retrieved from the 360 degrees of data. This allows the user to selectively reconstruct an appropriate 180 degrees of data that includes the desired cardiac cycle.

The regions 732 and 736 represent volumes that are partially illuminated by the cone beam 716 at each angular sampling position as the source 704 travels along the trajectory 708. The detected data in these regions includes between 180 and 360 degrees worth of data and, thus, can be reconstructed. However, this data may not be suitable for retrospective cardiac CT applications since it may not include the desired data. For example, before scanning the subject, the individual performing the scan does not know a priori which 180 degrees of the 360 degrees includes the desired cardiac phase. As a result, the detected data may or may not include the desired cardiac phase.

The regions 740 and 744 also represent volumes that are partially illuminated by the cone beam 716 as the source 704 travels along the trajectory 708. However, these regions include less than 180 degrees of data. As a result, this data cannot be reconstructed.

Figure 8:
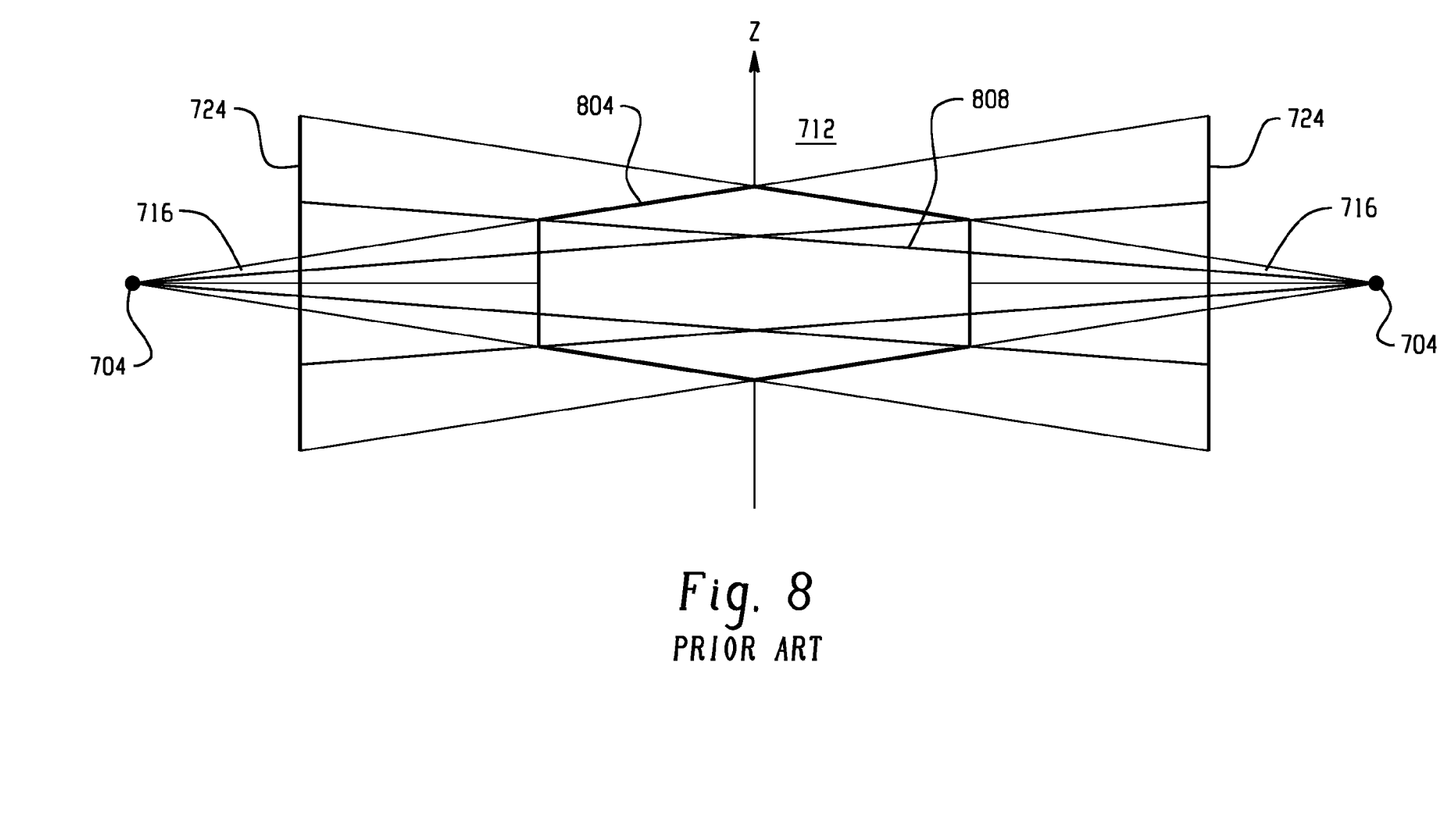

Another shortcoming of conventional cone beam axial CT is that only a subset of the reconstruction volume (the volume representing the regions 728, 732, and 736) can be suitably corrected or supplemented to improve image quality, for example, by reducing image artifact such as cone beam artifact, beam hardening artifact, metal artifact, etc. via iterative reconstruction techniques. This is illustrated in FIG. 8, which shows the source 704 emitting the cone beam 716 from a first position superimposed with the source 704 emitting the cone beam 716 from a second position, which is about 180 degrees apart from the first position relative to the z-axis. In this figure, a reconstruction volume 804 represents the regions 728, 732, and 736. Within the reconstruction volume 804, only a sub-volume 808 can be updated to reduce artifact due to the incomplete or limited data acquisition.

Figure 9:
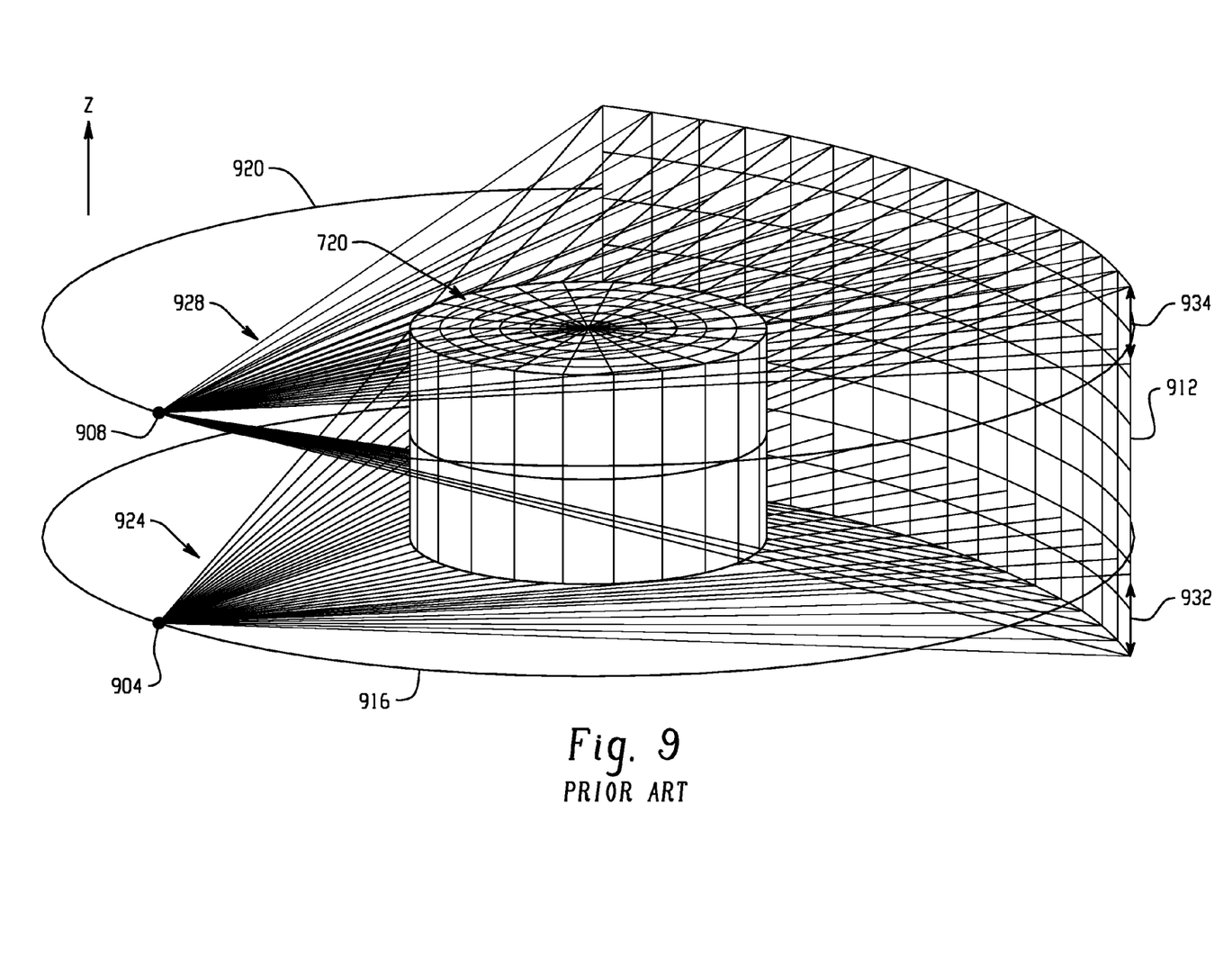
FIGS. 9 and 10 illustrate conventional stereo tube CT beam geometry.

The above discussed deficiencies with axial cone beam CT are mitigated by using two x-ray sources in a stereo tube configuration. As shown in FIG. 9, with a conventional stereo tube configuration two x-ray sources 904 and 908 are positioned at about the same angular position along different z-axis locations and share a common detector 912 for data acquisition. The x-ray sources 904 and 908 travel along trajectories 916 and 920 and alternately emit beams 924 and 928 that traverse the volume 720.

Figure 10:
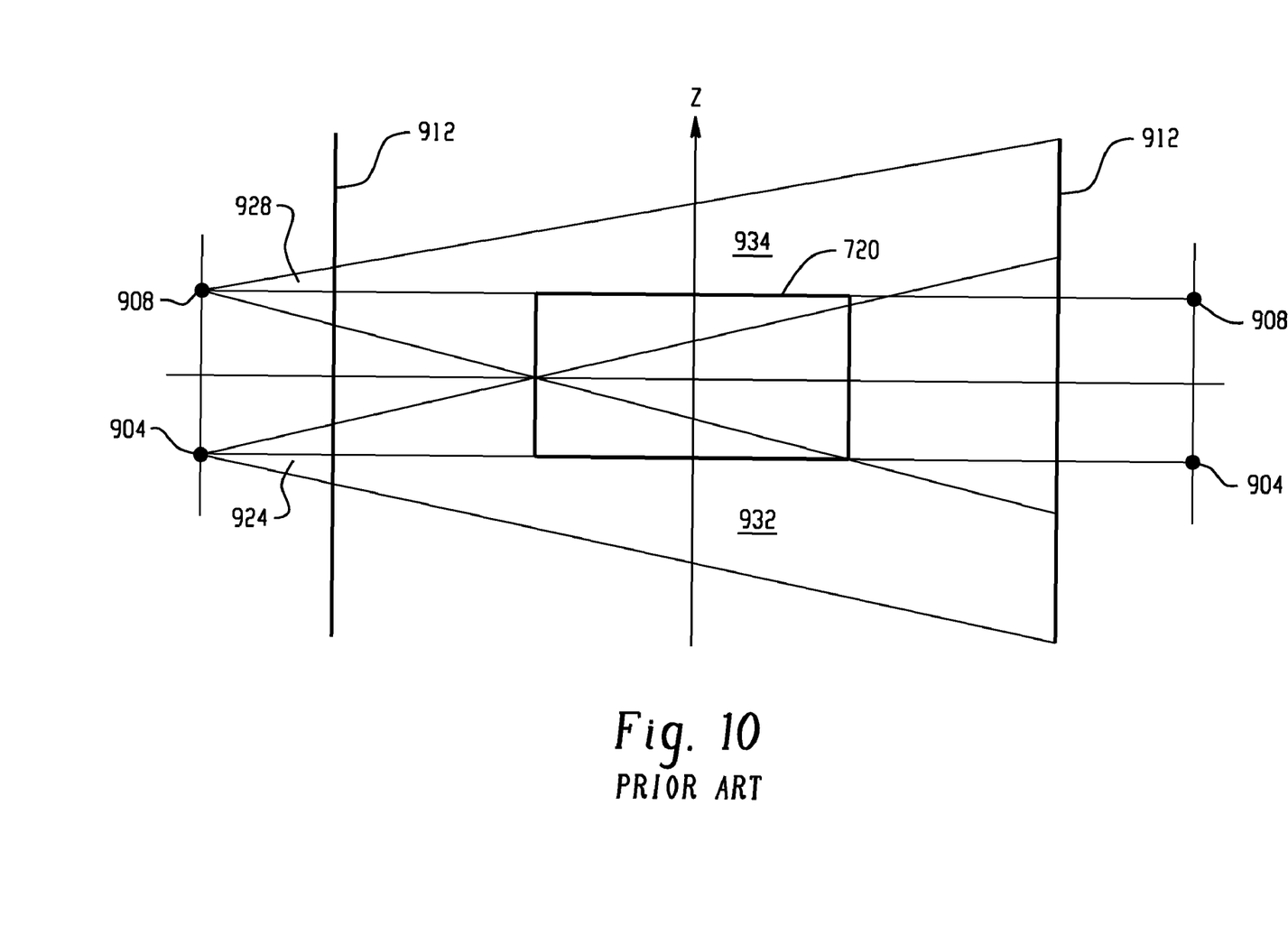

Configured as such, the combination of the beams 924 and 928 irradiate the entire volume 720 as the sources 904 and 908 rotate through the trajectories 916 and 920. As a result, at least 360 degrees of data is detected for the volume 720 as the sources 904 and 908 rotate through 360 degrees, and the entire volume 720 (or a subset thereof, if desired) is reconstructed. FIG. 10 shows that with stereo tube CT the entire volume 720 can be corrected with iterative correction techniques that use forward projection since a complete data set is available. For sake of clarity, the beams 924 and 928 are only shown at one angular position in FIG. 10.

Figure 6:
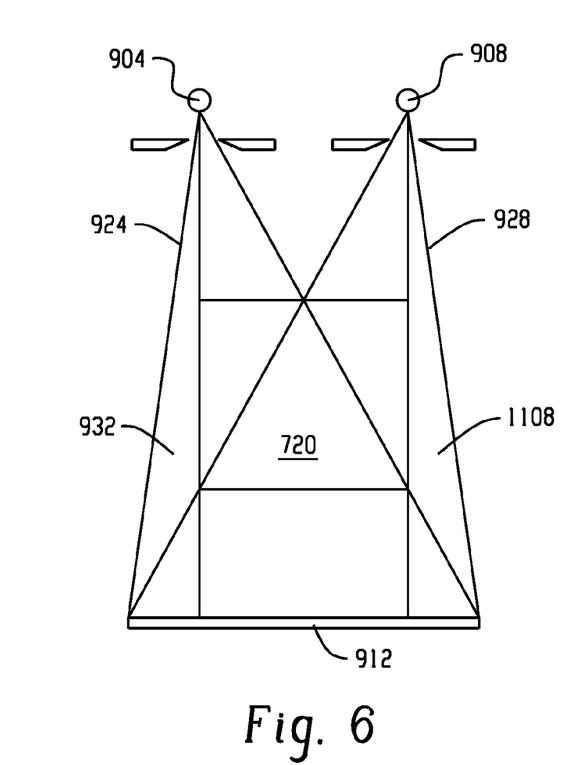
FIG. 6 illustrates conventional stereo tube CT beam geometry.

Unfortunately, with this configuration the beams 924 and 928 also irradiate regions outside of the reconstructed volume 720. This is shown in FIGS. 9 and 10 at 932 and 934, and is now discussed in connection with FIG. 6, wherein the beams 904 and 908 also irradiate the regions 932 and 934, which are outside of the reconstruction volume 720. X-rays traversing the regions 932 and 934 irradiate patient anatomy within these regions even though the corresponding detected data is not reconstructed. This results in inefficient dose utilization. Moreover, only one of the sources 904 and 908 irradiates the regions outside of the volume 720. Consequently, such regions (including the regions 932 and 934) are scanned using conventional axial cone beam CT, and the benefits of stereo tube CT are not available. Instead, these regions are susceptible to cone beam axial scan deficiencies in that the data is not suitably correctable or reconstructable.

In view of the above, there is an unresolved need for a stereo tube CT system with improved dose utilization.

Aspects of the present application address the above-referenced matters and others.

According to one aspect, a computed tomography system includes a first and a second source disposed at different z-axis locations at about a same angular position around an examination region that alternately emit radiation beams that traverse the examination region. The first source emits a first radiation beam having a first outer projection that traverses a plane perpendicular to the axis of rotation, and the second source emits a second radiation beam having a first outer projection that traverses a plane perpendicular to the axis of rotation. The first outer projections define a width of a volume within which the emitted radiation beams are confined. A common detector detects radiation from the x-ray beams that traverses the volume and generates data indicative thereof. A reconstructor reconstructs the data to generate an image of the volume.

According to another aspect, a stereo tube computed tomography system includes at least two sources disposed at different z-axis locations at about a same angular position around an examination region. A first source emits a first radiation beam having a first outer projection that traverses a plane perpendicular to the axis of rotation. A second source emits a second radiation beam having a first outer projection that traverses a plane perpendicular to the axis of rotation. A detector detects radiation from the x-ray beams that traverses a volume. A reconstructor reconstructs the data to generate volumetric image data corresponding to the volume.

According to another aspect, a computed tomography method is described. The method includes configuring a geometry of radiation beams emitted from different z-axis locations at about a same angular position around an examination region. A first beam has a first outer projection that travels perpendicular through an axis of rotation within the examining region and strikes a common detector. A second beam has a first outer projection that travels perpendicular through the axis of rotation within the examining region and strikes the common detector. The first outer projections define a volume that is irradiated by each of the beams. The method further includes detecting radiation from the x-ray beams that traverses a region irradiated by the radiation, and reconstructing the data to generate volumetric image data.

The invention may take form in various components and arrangements of components, and in various steps and arrangements of steps. The drawings are only for purposes of illustrating the preferred embodiments and are not to be construed as limiting the invention.

Figure 1:
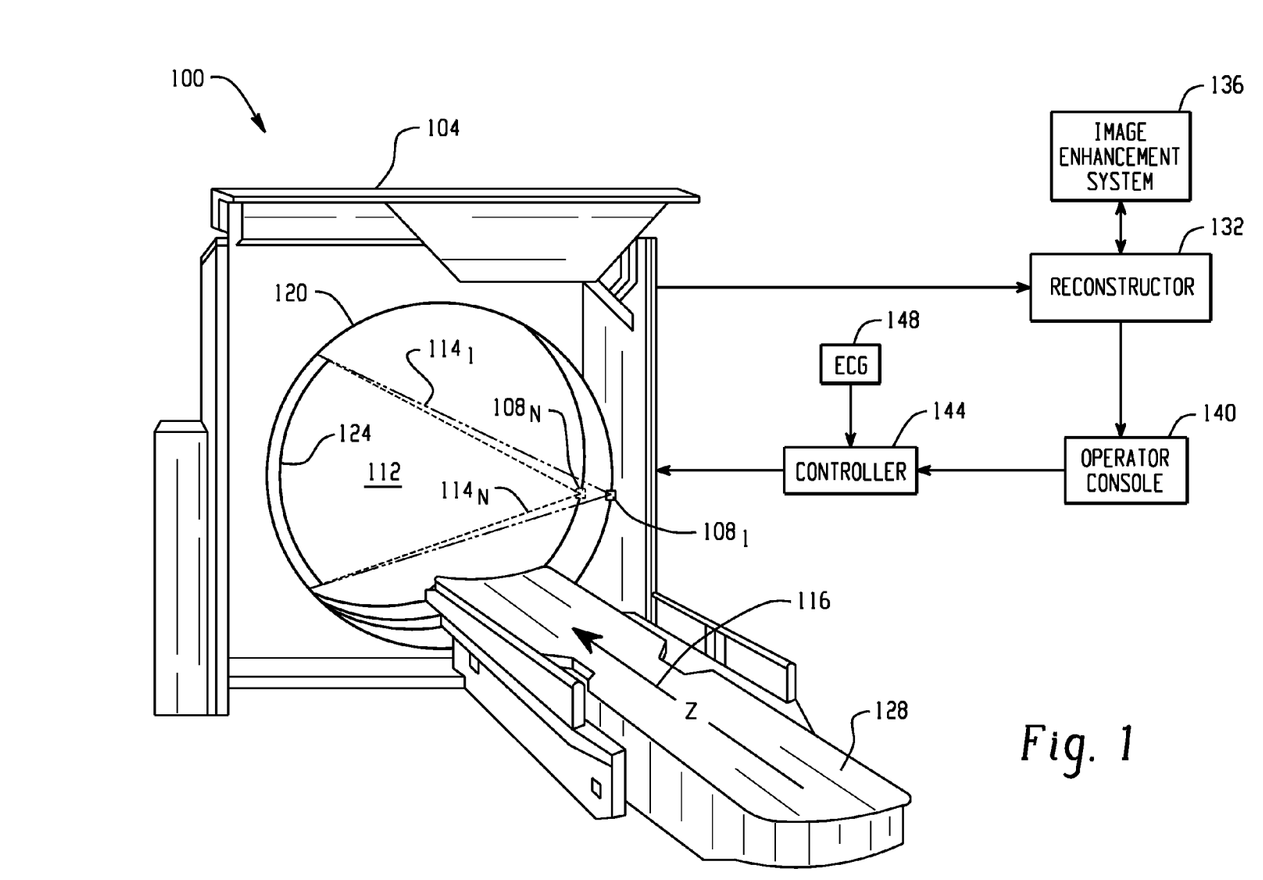
FIG. 1 illustrates an exemplary stereo tube CT imaging system employing a beam geometry that improves dose efficiency.

A medical imaging system 100 includes a scanner 104 having N x-ray sources $108_1$, $108_N$ (collectively referred to herein as x-ray sources 108), wherein N is an integer greater than one. As depicted, at least two x-ray sources 108 are disposed on a rotating gantry 120 at about a same angular position about an imaging region 112 and offset along a z-axis 116. The x-ray sources 108 are alternately activated such that only one of the sources 108 emits radiation at any given time. In this example, the x-ray sources 108 originate from different x-ray tubes.

The x-ray sources 108 are configured to generate radiation beams $114_1$, $114_N$ (collectively referred to herein as beams 114) having cone beam geometry. Other beam geometries such as fan beam are also contemplated herein. In one implementation, the geometry of the cone beams 114 defines a volume within the examining region 112 that is reconstructable in that the detected data indicative thereof includes enough samples for reconstruction purposes. For example, for a 360 degree axial scan the combination of the beams 114 generally irradiates the entire reconstruction volume throughout 360 degrees so at least 360 degrees of data is detected throughout the volume. As described in greater detail below, this beam geometry decreases or optimizes patient dose in that irradiation of patient anatomy outside of the reconstructed volume is reduced relative to conventional stereo tube CT techniques.

The scanner 104 further includes at least one detector 124. The detector 124 is a large area detector having a plurality of detector elements extending in the axial and transverse directions. When configured as such, the system 100 is able to image larger volumes relative to a one-dimensional or single slice detector systems. If desired, such capabilities can be leveraged to quickly acquire data representative of whole organs (e.g., the heart) or large portions thereof in a single axial scan. This facilitates acquiring high temporal resolution data with broad coverage in a short amount of time.

As depicted, the detector 124 subtends an angular arc opposite the x-ray sources 108. The imaging region 112 is defined therebetween. In one instance, the detector 124 rotates along with the x-ray sources 108, for example, as with a third generation CT system. In another instance, the system 100 includes a plurality of the detectors 124, each residing at a static angular location about a stationary gantry. In such instance, the detector 124 detecting radiation at any moment in time is determined by the angular position of the x-ray sources 108, for example, as with a fourth generation or e-beam CT system.

A support 128 supports the subject such as a human within the imaging region 112. The support 128 may be movable in order to guide the subject to a suitable location within the imaging region 112 before, during and/or after performing a helical, axial, and/or other scan, for example, by moving the support 128 along the z-axis 116 and/or one or more other axes.

A reconstructor 132 reconstructs the signals generated by the detector 124 and generates volumetric image data that is used to generate an image. An image enhancement system 136 is optionally used to supplement or correct the image data to reduce artifact. In one instance, the image enhancement system 136 uses an iterative reconstruction to reduce such artifact. With this approach, the image is forward projected to obtain projection data. The projection data is then compared with the measured projection data. In one instance, this comparison includes determining a difference between the calculated and measured data. The image is then updated based on the comparison. If desired or needed, multiple iterations are performed until the artifact is suitably reduced.

An operator console 148 facilitates user interaction with and/or control of the scanner 104. Software applications executed by the operator console 148 allow the user to configure and/or control operation of the scanner 104. For instance, the user can interact with the operator console 148 to select scan protocols, initiate, pause and terminate scanning, view images, manipulating volumetric image data, measure various characteristics of the data (e.g., CT number, noise, etc.), etc.

A controller 144 controls the x-ray sources 108. Such control includes, but is not limited to, activating and deactivating the x-ray sources 108. In addition, the controller 144 suitably adjusts beam geometry, if it is adjustable.

The illustrated embodiment is configured for retrospective cardiac CT applications and includes an ECG 152 for measuring and/or recording heart electrical activity while scanning a patient. The heart electrical activity is mapped to the resulting data. When the system is configured with the beam geometry described herein, 360 degrees worth of data is detected throughout the scan volume or volume of interest with a 360 degree axial scan. This enables the user to retrospectively select an arbitrary sub-set of data from the 360 degrees of data that includes a desired cardiac phase based on the recorded heart electrical activity. This subset is reconstructed and used to generate one or more images of the heart during the desired cardiac phase. It is to be appreciated that other physiological monitoring devices can alternatively or additionally be used to acquire information about the motion state of scanned anatomy.

Figure 2:
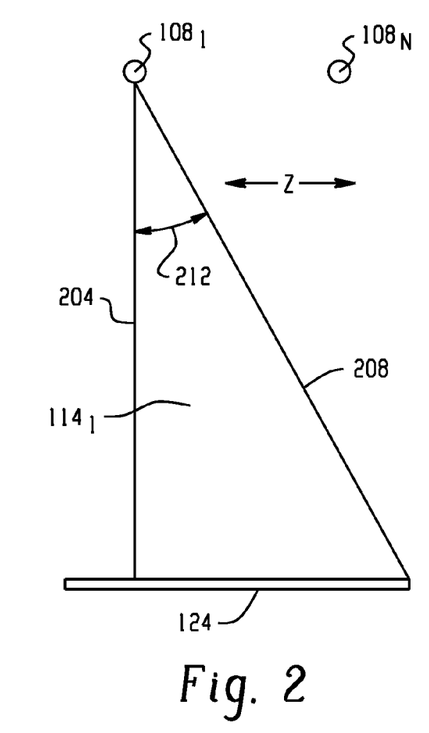
FIG. 2 illustrates an exemplary beam geometry for a first beam of the stereo tube CT system of FIG. 1.
Figure 3:
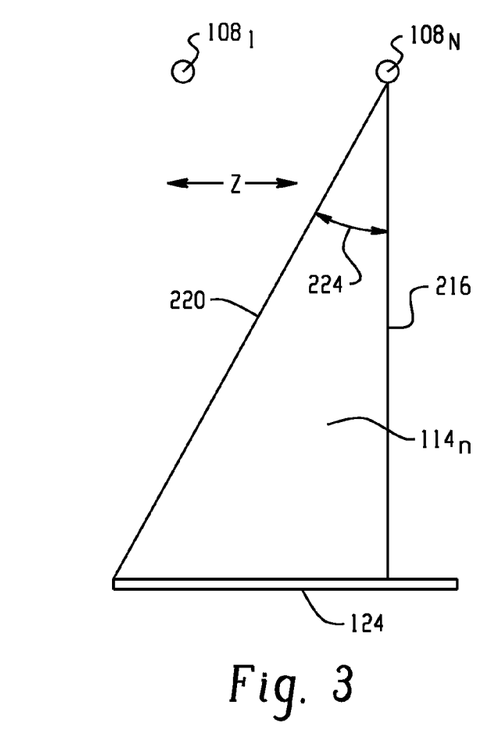
FIG. 3 illustrates an exemplary beam geometry for a second beam of the stereo tube CT system of FIG. 1.
Figure 4:
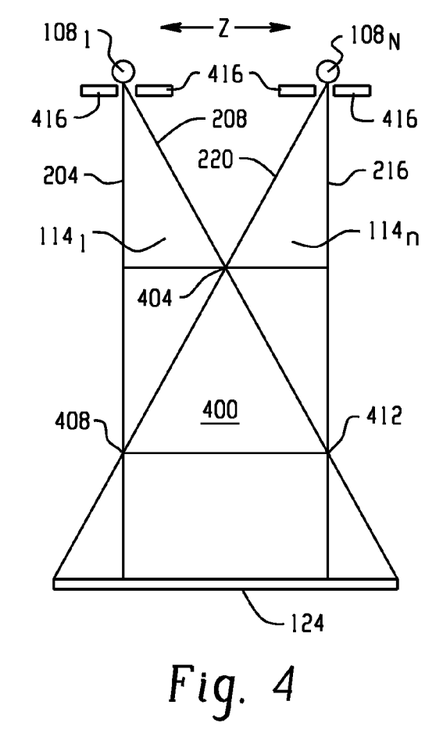
FIG. 4 illustrates a scan volume defined by the beam geometry through a superposition of the first and second beams described in connection with FIGS. 2 and 3.

FIGS. 2, 3, and 4 illustrate an exemplary beam geometry for efficient dose utilization. As discussed previously in connection with FIGS. 9, 10, and 11, conventional stereo tube CT beam geometry results in irradiation of regions outside of the reconstructed volume 720, which results in inefficient dose utilization since patient anatomy is irradiated, but these region are not reconstructed.

In FIG. 2, the geometry of the x-ray beam $114_1$ is configured such that a first outer projection 204 travels along a plane perpendicular to the z axis or an axis of rotation and strikes the detector 124 away from the end of the detection surface. A second outer projection 208 of the x-ray beam $114_1$ travels at an angle 212 relative to the first outer projection 204 and strikes the detector 124. In this example, the first outer projection 204 and the second outer projection 208 define or follow a contour or perimeter of the beam $114_1$ such that the remaining x-rays in the beam $114_1$ are substantially or largely bound by, confined within, or between the first and second outer projections 204 and 208. The width of the beam $114_1$ is defined through the angle 212 and is configured in this example such that the second outer projection 208 strikes the detector 124 near the end of the detection surface. As a result, the beam $114_1$ asymmetrically illuminates the detector 124 about a longitudinal or axial midpoint of the detector 124.

In FIG. 3, the geometry of the x-ray beam $114_N$ is also configured so that a first outer projection 216 travels along a plane perpendicular to an axis of rotation and strikes the detector 124 away from the end of the detection surface. A second outer projection 220 of the x-ray beam $114_N$ travels at an angle 224 relative to the first outer projection 216 and strikes the detector 124. Similarly, the first outer projection 216 and the second outer projection 220 define or follow a contour or perimeter of the beam $114_N$ such that the remaining x-rays in the beam $114_N$ are substantially or largely bound by confined within, or between the first and second outer projections 216 and 220. The width of the beam $114_N$ is defined through the angle 224 such that the second outer projection 220 strikes the detector 124 near the end of the detection surface. The outer projections 216 and 220 strike the detector 124 such that the beam $114_N$ asymmetrically illuminates the detector 124 about a midpoint of the detector 124.

FIG. 4 illustrates a superposition of the beams $114_1$ and $114_N$ relative to the detector 124. As shown, the first outer projections 204 and 216 the beams 114 define a z-axis extent of a reconstruction volume 400 within the examining region 112, which is the region irradiated. The second outer projections 208 and 220 cross or intersect at a perimeter or midpoint 404 of the volume 400 on a side of the volume 400 proximate the sources 108. The first outer projection 204 of the first beam $114_1$ and the second outer projection 216 of the second beam $114_N$ cross or intersect at a first corner 408 of the volume 400, and the second outer projection 208 of the first beam $114_1$ and the first outer projection 216 of the second beam $114_N$ cross or intersect at a second corner 412 of the volume 400.

With this geometry, the z-axis extent of the volume 400 is irradiated by both of the beams 114 throughout an axial scan and regions outside of the volume 400 are substantially un- irradiated by the beam 114. As a result, the data indicative of the volume 400 includes at least 360 degrees worth of data. However, unlike the conventional stereo tube CT beam geometry in FIGS. 9, 10, and 11, the geometry of the beams 114 is configured so that the beams 114 do not irradiate regions outside of the volume 400. As discussed above, this reduces patient dose relative to conventional stereo tube CT beam geometry.

By asymmetrically illuminating the detectors 124, the beam geometry described herein efficiently utilizes the detector 124 since the beams 114 are configured to strike the portion of the detector 124 corresponding to width of the reconstructed volume 400 rather than arbitrarily cover the entire width of the detector 124.

Exemplary alternative embodiments are described next.

It is to be appreciated that in an alternative embodiment, the x-ray sources 108 are disposed on the gantry 120 offset along the z-axis 116 and at different angular positions about an imaging region 112. In this embodiment, different detectors are used to detect radiation emitted by each of the sources 108 at any given time. One advantage to such embodiment is that the sources 108 can be simultaneously activated to emit radiation, which can improve the spatial or temporal resolution since more data is detected in the same amount of time.

In another embodiment, each of the x-ray sources 108 is moveable along the z-axis. For instance, the x-ray sources 108 can be mechanically or electronically moveable along the z-axis. With such embodiment, the sources 108 and their geometry (e.g., beam angles or widths) are adjusted to conform to different volumes or regions of interest.

The x-ray sources 108 in the illustrated system 100 originate within separate x-ray tubes attached to the gantry 120. However, in another embodiment the x-ray sources 108 originate from different foci within the same x-ray tube. In yet another embodiment, the system 100 includes a plurality of x-ray sources 108 in which a combination of single and multi foci tubes are employed. In still another embodiment, the x-ray sources 108 are generated by an electron beam generator or gun that controls the position of the e-beam through electronic deflection or the like.

In the illustrated embodiment, the geometry of the cone beams defines the volume within the examining region 112 that is reconstructed. In an alternative embodiment, the beam angles 212 and 224 and/or shape are adjusted so that the beams 114 conform to a desired volume of interest, for example, so that they follow a contour or perimeter of a desired volume. In one implementation, beam collimators 416 or the like control the beam shape and the angles 212 and 224.

In another embodiment, the x-ray sources 108 are simultaneously activated to concurrently emit x-rays. In such embodiment, the system 100 employs a component or techniques for separating the data by among the contributing sources or employing a reconstruction technique that takes into consideration the multiple source.

It is also to be understood that scans less than 360 degrees such at 180 degree scans are also contemplated herein. Such scans may result in 180 degrees plus a fan angle worth of data, which can be reconstructed using a 180 reconstruction technique.

Figure 5:
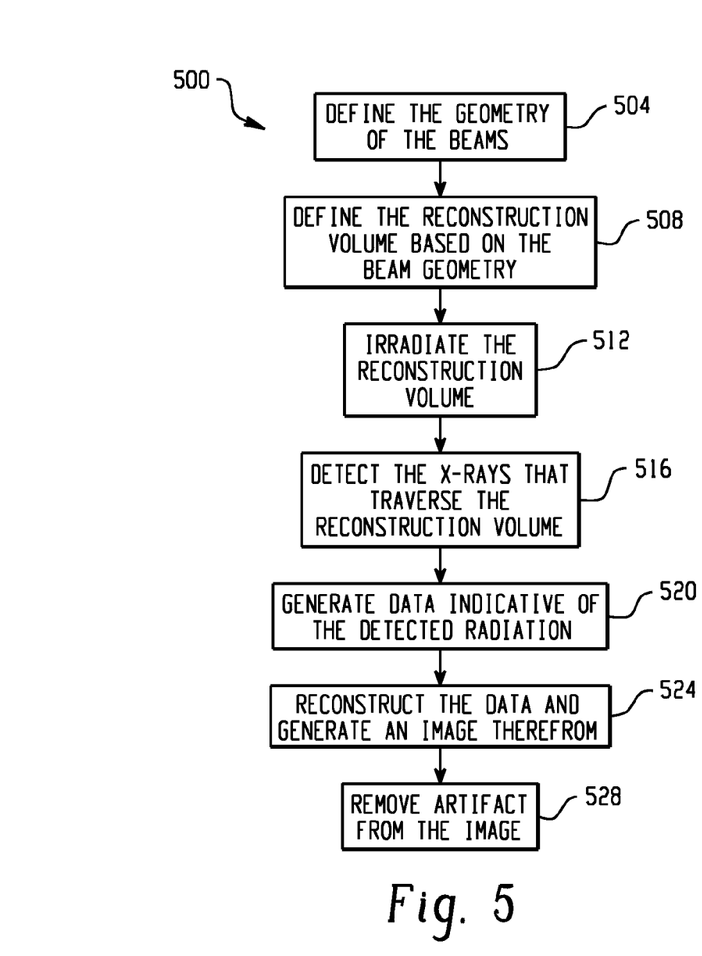
FIG. 5 illustrates an exemplary method for using the system described in FIG. 1.

FIG. 5 illustrates an exemplary method 500 that improves dose efficiency in a stereo tube CT system. At reference numeral 504, the geometry of each of the beams is defined as described above. At 508, a scan volume within the examining region is defined based on the beam geometry. Alternatively, a desired scan volume can be defined and the beam geometry can be selected to substantially conform to the desired volume of interest. At 512, the scan volume is substantially entirely irradiated with x-rays as a result of the beam geometry. The geometry of the beams keeps the x-rays within the boundary of the scan volume to mitigate irradiating regions not reconstructed and reduce patient dose. At 516, the x-rays that traverse the scan volume are detected. At 520, signals indicative of the detected x-rays are reconstructed. At 524, the reconstructed data is used to generate an image of the scan volume. Optionally, at 528, the image data is supplemented to improve image quality through an iterative reconstruction technique.

It is to be appreciated that the system 100 is suited for applications such as cardiac CT, perfusion imaging, functional imaging, metabolic imaging, and the like.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A computed tomography system, comprising:
a first and a second x-ray tube, disposed at different z-axis locations at about a same angular position around an examination region, that both emit, alternatively, radiation beams, during an axial scan, that traverse an axis of rotation within the examination region;
wherein the first x-ray tube emits a first radiation beam having a first outer projection that traverses a plane perpendicular to the axis of rotation, and the second x-ray tube emits a second radiation beam having a first outer projection that traverses a plane perpendicular to the axis of rotation, wherein the first outer projections define a width of a volume within which the emitted radiation beams are substantially bound;
a common detector that detects radiation from the x-ray beams that traverses the volume and generates data indicative thereof; and
a reconstructor that reconstructs the data to generate volumetric image data of the volume.

2. The system of claim 1, wherein each of the radiation beams traverse substantially all of the width of the volume as the x-ray tubes rotate around the examination region over a single revolution.

3. The system of claim 1, wherein each of the first radiation beam and the second radiation beam asymmetrically illuminates the detector about a longitudinal midpoint of the detector.

4. The system of claim 1, wherein a beam angle is configured to define beams with widths that contour the z-axis width of the volume at a perimeter of the volume on a detector side of the examination region.

5. The system of claim 1, wherein a second outer projection of the first beam and a second outer projection of the second beam traverse paths that intersect at about a center at a perimeter of the volume on a side of the examination region proximate the x-ray tube.

6. The system of claim 5, where the first outer projection and the second outer projection of the first beam define a perimeter of the first beam, and the first outer projection and the second outer projection of the second beam define a perimeter of the second beam.

7. The system of claim 1, wherein the data indicative of the volume includes at least 180 degrees plus a fan angle of data.

8. The system of claim 1, wherein the data indicative of the volume includes at least 360 degrees of data.

9. The system of claim 1, further including an ECG device that records heart electrical activity when scanning a patient, wherein the heart electrical activity is mapped to the detected data and utilized to select a subset of the data that includes a desired cardiac phase.

10. The system of claim 1, further including generating an image from the volumetric image data and further including an image enhancement system that employs an iterative reconstruction technique to reduce artifact in the image.

11. The system of claim 9, wherein the image enhancement system forward projects the image, compares the forwarded projected data with measured data, and updates the image based on the comparison to reduce image artifact.

12. The system of claim 1, wherein the radiation emitted by the x-ray tubes irradiates a sub-portion of a patient being scanned that is within the volume and does not irradiate any sub-portion of the patient the is outside of the volume.

13. A computed tomography method, comprising:
using only first and a second x-ray tubes disposed at different z-axis locations at about a same angular position around an examination region to emit radiation beams that traverse an axis of rotation within the examination region;
wherein the first x-ray tube emits a first radiation beam having a first outer projection that traverses a plane perpendicular to the axis of rotation, and the second x-ray tube alternately emits a second radiation beam having a first outer projection that traverses a plane perpendicular to the axis of rotation, wherein the first outer projections define a width of a volume within which the emitted radiation beams are substantially bound;
detecting the radiation that traverses the volume with a common detector and generating data indicative thereof, wherein a substantial portion of each of the first and second radiation beams irradiates a same substantial portion of the common detector; and
reconstructing the data with a reconstructor to generate volumetric image data of the volume.

14. A computed tomography system, comprising:
at least two sources disposed at different z-axis locations at different angular positions around an examination region, that emit radiation beams that traverse an axis of rotation within the examination region;
wherein a first source emits a first radiation beam having a first outer projection that traverses a plane perpendicular to the axis of rotation, and a second source emits a second radiation beam having a first outer projection that traverses a plane perpendicular to the axis of rotation, wherein the first outer projections define a width of a volume within which the emitted radiation beams are substantially bound;
at least two detectors, wherein one of the detectors detects radiation from the first source and the other of the detectors detects radiation from the second source; and
a reconstructor that reconstructs the radiation to generate volumetric image data of the volume.

15. A stereo tube computed tomography system, comprising:
at least two sources disposed at different z-axis locations at about a same angular position around an examination region;
wherein a first source emits a first radiation beam having a first outer projection that traverses a plane perpendicular to the axis of rotation, and a second source emits a second radiation beam having a first outer projection that traverses a plane perpendicular to the axis of rotation; wherein the first outer projection sources follow a contour of an irradiated volume;

a detector that detects radiation from the x-ray beams that traverses the volume; and a reconstructor that reconstructs the data to generate volumetric image data corresponding to the volume.

16. The system of claim 15, wherein the first outer projections define a z-axis width of the volume.

17. The system of claim 15, wherein the first outer projections of the first beam is configured to follow a first z-axis boundary of the volume and the first outer projections of the second beam is configured to follow a second z-axis boundary of the volume.

18. The system of claim 15, wherein each of the first radiation beam and the second radiation beam combine to irradiate the entire volume as the sources rotate around the examination region.

19. The system of claim 15, wherein a second outer projection of the first beam and a second outer projection of the second beam cross at a first side of the volume, the first outer projection of the first beam and the second outer projection of the second beam cross at a first corner of the volume, and the second outer projection of the first beam and the first outer projection of the second beam cross at a second corner of the volume.

20. The system of claim 15, further including at least two x-ray tubes or an x-ray tube with at least two foci, wherein each of the at least two sources is generated by a different x-ray tube or a different focal spot.

21. A stereo tube computed tomography method, comprising:

configuring a first outer projection of a first beam of a first x-ray tube to travel perpendicular to an axis of rotation within the examining region;

configuring a first outer projection of second beam of a second x-ray tube to travel perpendicular to the axis of rotation within the examining region; wherein the first outer projections define a z-axis region to irradiate; and configuring beam angles to localize the beams to substantially irradiate an extent of the z- axis region during axial scanning;

wherein the radiation beams are located at different z-axis locations at about a same angular position around an examination region.

22. The method of claim 21, further including using information from a physiological monitoring device to perform a motion gate examination.

23. The method of claim 21, further including using an iterative reconstruction to adjust the image data to reduce one or more of cone beam, beam hardening, and metal artifact.

* * * * *